United States Patent [19]

Wingen et al.

[11] Patent Number: 4,985,172

[45] Date of Patent: Jan. 15, 1991

[54] CHIRAL ARYLOXYPROPIONATES, AND THE USE THEREOF AS DOPES IN LIQUID-CRYSTAL PHASES

[75] Inventors: Rainer Wingen, Hattersheim am Main; Hans-Rolf Dübal, Hofheim am Taunus; Wolfgang Hemmerling, Sulzbach; Ingrid Müller, Hofheim am Taunus; Dieter Ohlendorf, Liederbach, all of Fed. Rep. of Germany

[73] Assignee: Hoechst AG, Fed. Rep. of Germany

[21] Appl. No.: 359,747

[22] PCT Filed: Nov. 2, 1987

[86] PCT No.: PCT/EP87/00653

§ 371 Date: May 5, 1989

§ 102(e) Date: May 5, 1989

[87] PCT Pub. No.: WO88/03525

PCT Pub. Date: May 19, 1988

[30] Foreign Application Priority Data

Nov. 8, 1986 [DE] Fed. Rep. of Germany ....... 3638119

[51] Int. Cl.$^5$ .................. C09K 19/20; C07D 239/02; C07C 69/76

[52] U.S. Cl. ..................... 252/299.67; 252/299.66; 252/299.65; 252/299.64; 252/299.61; 252/299.01; 350/350 S; 544/298; 544/335; 560/59; 560/61; 560/73

[58] Field of Search ............... 252/299.01, 299.61, 252/299.64, 299.65, 299.66, 299.67; 350/350; 544/298, 335; 560/59, 61, 73

[56] References Cited

U.S. PATENT DOCUMENTS

| | | | |
|---|---|---|---|
| 4,744,918 | 5/1988 | Hepple et al. | 252/299.61 |
| 4,775,223 | 10/1988 | Yoshinaga et al. | 252/299.01 |
| 4,820,839 | 4/1989 | Krause et al. | 252/299.61 |
| 4,824,217 | 4/1989 | Chan et al. | 252/299.01 |
| 4,852,977 | 8/1989 | Chan et al. | 350/350 S |
| 4,866,199 | 9/1989 | Shibata et al. | 560/65 |
| 4,876,026 | 10/1989 | Saito et al. | 252/299.61 |
| 4,882,084 | 11/1989 | Ohno et al. | 252/299.66 |

FOREIGN PATENT DOCUMENTS

| | | |
|---|---|---|
| 259995 | 3/1988 | European Pat. Off. |
| 317204 | 5/1989 | European Pat. Off. |
| 62-198647 | 9/1987 | Japan |
| 86/02937 | 5/1986 | World Int. Prop. O. |
| 87/05012 | 8/1987 | World Int. Prop. O. |

Primary Examiner—John S. Maples
Assistant Examiner—Richard Treanor
Attorney, Agent, or Firm—Bierman and Muserlian

[57] ABSTRACT

Arylcarboxylates of 2-hydroxypropionates are known, amongst other compounds, as dopes for converting tilted smectic liquid-crystal phases into ferroelectric liquid-crystal phases.

The novel chiral aryloxypropionates of the general formula

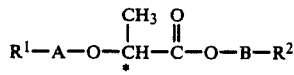

are two-fold chiral and in which the symbols have the following meaning:

$R^1$ denotes a straight-chain alkyl or alkoxy radical having 1 to 16 carbon atoms or a branched alkyl or alkoxy radical having 4 to 16 carbon atoms, it being possible for one or two non-adjacent $CH_2$ groups to be replaced by a sulfur and/or oxygen atom;

A denotes one, two or three aromatic or heteroaromatic rings which are linked to one another directly or via one or two COO groups;

B denotes a chemical bond or one or two aromatic or heteroaromatic rings which are linked directly to one another;

$R^2$ (a) if B is a chemical bond, denotes an alkyl radical having 2 to 10 carbon atoms which contains an asymmetrical carbon atom which is substituted by $CH_3$, halogen or a $COOC_2H_5$ group, or an alkyl radical having 3 to 10 carbon atoms which contains two adjacent, asymmetrical carbon atoms of which one is substituted by halogen and the other by a $CH_3$ group, or which, together with an O, form an oxirane ring, or (b) if B denotes one or two aromatic or heteroaromatic rings which are bonded directly to one another, denotes alkoxy radicals having the same number of carbon atoms and the same structure of the alkyl group as under (a).

9 Claims, No Drawings

CHIRAL ARYLOXYPROPIONATES, AND THE USE THEREOF AS DOPES IN LIQUID-CRYSTAL PHASES

Especially in the last decade, liquid crystals have been introduced into a very wide variety of industrial areas in which electrooptical and display device properties are in demand (e.g. in displays for watches, pocket calculators and typewriters). These display devices are based on dielectric alignment effects in nematic, cholesteric and/or smectic phases of liquid-crystalline compounds, where—caused by the dielectric anistropy—the longitudinal molecular axis of the compounds adopts a preferred alignment in an applied electrical field. The usual switching times in these display devices are rather too slow for many other potential areas of application of liquid crystals, which are per se very promising chemical compounds for industry due to their unique properties. This disadvantage is particularly noticeable when—which is necessaily the case in relatively large display element areas—it is necessary to address a large number of image points, which means that the production costs of equipment containing relatively large areas, such as video equipment, oscillographs or TV, radar, EDP or word processor screens, would be too high.

Besides nematic and cholesteric liquid crystals, tilted smectic liquid-crystal phases have in the last few years also become increasingly important. If suitable dopes which exhibit or induce in the liquid-crystal phase so-called spontaneous polarization ($P_s$) are added to such tilted smectic phases, in particular smectic C ($S_c$ or SmC) phases, the phases can be converted into ferroelectric liquid-crystal phases (denomination of $P_s$ in $nC.cm^{-2}$), in this respect, see, for example, Lagerwall et al. in the paper "Ferroelectric Liquid Crystals for Displays", SID Symposium, Oct. Meeting, 1985, San Diego (USA). Compared with customary TN ("twisted nematic") cells, these FLC phases have switching times which are faster by a factor of about 1,000. As a consequence of these and other positive properties, such as the possibility of bistable switching, they are good potential candidates for the abovementioned areas of application (for example via matrix addressing).

In WO-A 86/02937, compounds of the formula below

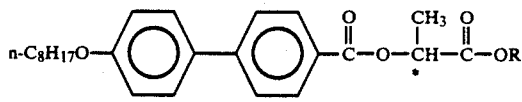

which are 2-hydroxypropionates esterified on the hydroxyl group by arylcarboxylic acids and in which R may denote methyl, ethyl, propyl or n-butyl, are described, amongst others, as components of ferroelec-tric liquid-crystal mixtures.

The spontaneous polarization $P_s$ for these compounds (determined in a 10 mol-% mixture with racemic CE 8) is given as 72.6 $nC.cm^{-2}$ (extrapolated to the pure substance) at a temperature 10° below the $S_c^*-S_A$ transition; neither switching times nor other application-relevant parameters are given.

In EP-A 0,175,591, compounds of the formula below

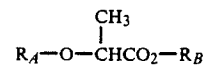

in which the symbols have the following meaning:
$R_A$: a linear, branched or cyclic, saturated or unsaturated hydrocarbon radical having 1 to 20 carbon atoms;
$R_B$:

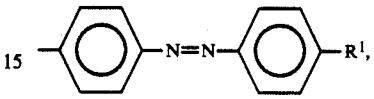

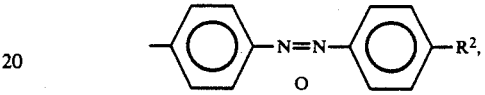

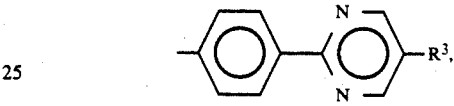

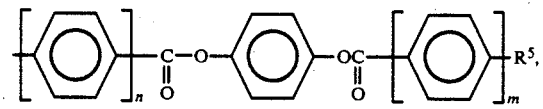

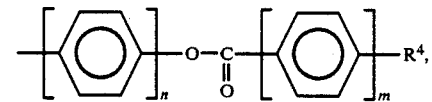

where $R^1$ to $R^5$ denote alkyl or alkoxy groups having 1 to 20 carbon atoms and n and m denote 1 or 2, are described, amongst other compounds, as components of liquid-crystal mixtures. These compounds are described as being advantageous for achieving bistable behavior in ferroelectric liquid-crystal mixtures; optically active carbon atoms in $-R_B$ are not mentioned.

In WO-A 87/05012, which is not a prior publication, aryloxypropionic acid esters are described, but these differ from the compounds according to the invention in that the alkyl radical or alkoxy radical at the right-hand end of the molecule in the WO-A denotes $C_1$- to $C_{12}$-alkyl or $C_1$- to $C_{12}$-alkyloxy. Although it is stated (page 2, lines 31 to 34) that this alkyl group may be straight-chain, branded or "chiral", consideration of concrete compounds from Table 3 (p.4) and the definition for "$R_2$" (page 5, lines 2 to 4) shows that, however, only asymmetric carbon atoms which are linked to the remainder of the molecule via a carboxyl group come under the definition of $R^2$.

The invention relates to compounds which, with high values for inherent spontaneous polarization $P_s$ or spontaneous polarization $P_s$ induced in liquid-crystal phases, have structural elements which also render them "compatible", i.e. miscible, with other components in liquid-crystal systems, in particular with ester compounds having a $S_c$ phase or with phenylpyrimidine compounds having a $S_c$ phase, since, inter alia, the mesogenic part of the molecules is often responsible for good "compatibility" with the other mixture components in liquid-crystal systems. At the same time, these compounds need not necessarily be liquid-crystalline themselves, and in particular need not necessarily have a SmC phase.

The invention also relates, in particular, to the novel compounds collated in the table.

The chiral aryloxypropionates according to the invention are compounds of the formula (I); in the general formula (I),

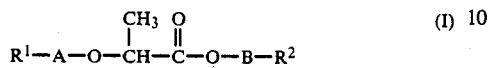

$R^1$, A, B and $R^2$ have the following meaning:

$R^1$ denotes a straight-chain alkyl or alkoxy radical having 1 to 16 carbon atoms or a branched alkyl or alkoxy radical having 4 to 16 carbon atoms, it being possible for one or two non-adjacent $CH_2$ groups to be replaced by a sulfur and/or oxygen atom;

A denotes one, two or three aromatic or heteroaromatic rings which are linked to one another directly or via one or two COO group(s);

B denotes a chemical bond or one or two aromatic or heteroaromatic rings which are linked directly to one another;

$R^2$ (a) if B is a chemical bond, denotes an alkyl radical having 2 to 10 carbon atoms which contains an asymmetrical carbon atom which is substituted by $CH_3$, halogen or a $COOC_2H_5$ group, or an alkyl radical having 3 to 10 carbon atoms which contains two adjacent, asymmetrical carbon atoms of which one is substituted by halogen and the other by a $CH_3$ group, or which, together with an O, form an oxirane ring, or (b) if B denotes one or two aromatic or heteroaromatic rings which are linked directly to one another, denotes alkoxy radicals having the same number of carbon atoms and the same structure of the alkyl group as under (a).

In the case of A, the aromatic ring should preferably be taken to mean a 1,4-phenylene group, and the heteroaromatic ring should preferably be taken to mean a pyrimidine-2,5-diyl radical. Compounds in which two 1,4-phenylene rings are bonded to one another via a carbonyloxy group or three 1,4-phenylene rings via two carbonyloxy groups are likewise preferred.

In the case of B, the aromatic ring should preferably be taken to mean a 1,4-phenylene group, and the heteroaromatic ring should preferably be taken to mean a pyrimidine-2,5-diyl. Compounds in which B represents a direct bond between the ester O atom and $R^2$ are also preferred.

Particularly preferred chiral aryloxypropionates are compounds in which $R^1$, A and B in the formula (I) have the following meanings:

$R^1$ denotes a straight-chain alkyl or alkoxy radical having 7 to 16 carbon atoms, A denotes a phenylene, biphenylene, pyrimidinephenyl, phenylcarbonyloxyphenyl or [(phenylcarbonyloxy)-phenylcarbonyloxy]phenyl radical, and B denotes a chemical bond, or a phenylene, biphenylene or pyrimidinephenyl radical.

The compounds of the general formula (I) according to the invention are two-fold chiral and can be prepared, for example, as shown in scheme 1, by reacting a mesogenic phenol (II) with a chiral propionic acid compound (III) to give a chiral aryloxy compound (IV), which is then converted into the chiral aryloxypropionic acid (V) by base or acid-catalyzed hydrolysis; esterification of (V) by means of the hydroxyl compound (VI) produces the compound (I) according to the invention.

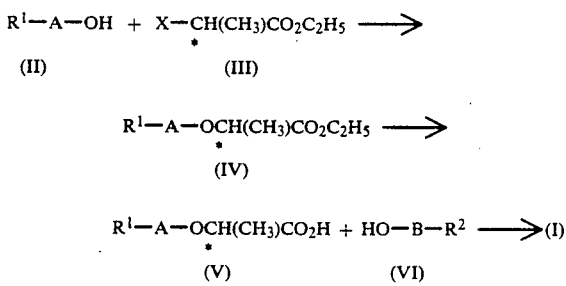

The educts (II) and (VI) are known from the literature, as is$ the chiral propionic acid derivative (III), in which X may have the following meaning: OH, halogen, 4-toluenesulfonyloxy, methylsulfonyloxy or trifluoromethylsulfonyl.

The processes using which the compounds (II) and (III) are linked to one another without racemization to form the compounds (IV) are likewise known to those skilled in the art from the literature.

Thus, alkali metal phenoxides can be reacted with 2(sulfonyloxy)carboxylic acid compounds to form phenoxycarboxylic acid compounds with retention of the chirality, as described by Burkard and Effenberger, "Racemizationfree substitution of 2-(sulfonyloxy)carboxylates using oxygen- and sulfur-based nucleophiles", in Chem. Ber. 119, 1594–1612 (1986).

The reaction of phenols with alcohols to give phenol (sic) alkyl ethers with the aid of diethyl azodicarboxylate and triphenyl phosphine, as described by Mitsonobu, "The Use of Diethyl Azodicarboxylate and Triphenyl Phosphine in the Synthesis and Transformation of Natural Products", in Synthesis 1981, 1–28, can also be used for the preparation of (IV), and thus ultimately of (I), if anethylanlactate (III, X=OH) is reacted with a mesogenic phenol (II).

The hydrolysis of (IV) to give (V) and the esterification of (V) using (VI) to give (I) can be carried out by methods which are known to those skilled in the art.

The invention also relates to twistable liquid-crystal phases containing at least one chiral compound which contain, as chiral compound, at least one compound of the general formula (I). The term "twistable liquid-crystal phase" is taken to mean nematic, cholesteric or tilted smectic, in particular SmC, phases.

The twistable liquid-crystal phases comprise 2 to 20, preferably 2 to 15, components, including at least one of the two-fold chiral compounds claimed in the invention. The other components are preferably selected from known compounds having nematic, cholesteric and/or twisted smectic phases, which include, for example, Schiff bases, biphenyls, terphenyls, phenylcyclohexanes, cyclohexylbiphenyls, pyrimidines, cinnamates, esters of cholesterol, and various bridged terminal-polar multinuclear esters of p-alkylbenzoic acids. In general, the commercially available liquid-crystal phases exist, even before addition of the chiral compound(s), as mixtures of a very wide variety of components of which at least one is mesogenic, i.e. exhibits a liquid-crystal phase as the compound, in derivatized form or mixed with certain cocomponents, i.e. at least one enantiotropic (clear point > melting point) or monotropic (clear point < melting point) mesophase formation is to be expected.

In particular, the twistable liquid-crystal phase contains, besides at least one of the two-fold chiral compounds claimed in the invention, an ester compound having an S$_c$ phase, for example a phenyl 4-alkoxybenzoate, or a phenyl pyrimidine compound having an S$_c$ phase, for example a 4-(5-alkylpyrimidin-2-yl)-1-alkoxybenzene. The liquid-crystal phases generally contain 0.01 to 70% by weight, in particular 0.05 to 50% by weight, of the compound(s) according to the invention.

The compounds according to the invention are suitable, in particular, as dopes for tilted smectic liquid-crystal phases since they convert the latter into ferroelectric liquid-crystal phases; the values for spontaneous polarization (Ps) are in the range from about 10 to 120 nC.cm$^{-2}$ (extrapolated linearly to the pure compound).

PREPARATION EXAMPLES

A Octyl (R)-(+)-2-[4-(5-octylpyrimidin-2-yl)phenyl]oxypropionate I, R$^1$:C$_8$H$_{17}$,

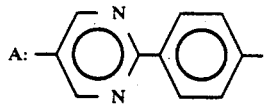

B: —, R$^2$:C$_8$H$_{17}$)

5.25 g (0.02 mmol) of triphenyl phosphine and 3.15 ml (0.02 mol) of diethyl azodicarboxylate are dissolved in 75 ml of tetrahydrofuran at 0° C. After 15 minutes, 5.69 g (0.02 mol) of 4-(5-octylpyrimidin-2-yl)phenol (II, R$^1$:C$_8$H$_{17}$,

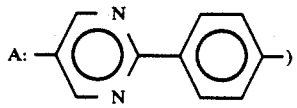

and 2.36 g (0.02 mol) of ethyl (S)-(−)-lactate (III, X:OH) are added. After 16 hours, the mixture is evaporated to dryness in vacuo, and the residue is chromatographed over 200 g of silica gel using dichloromethane as the eluent. 5.7 g (74%) of a colorless oil are produced (IV, R$^1$:C$_8$H$_{17}$,

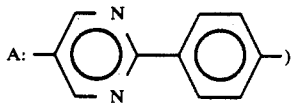

The oil is taken up in 30 ml of methanol, and 33% strength sodium hydroxide solution is added dropwise at 15° C. until precipitation no longer occurs on addition of the lye and the ester (IV) can no longer be detected by thin-layer chromatography. The pH is adjusted to 2 by adding 10 N HCl, and the precipitated acid (V, R$^1$:C$_8$H$_{17}$,

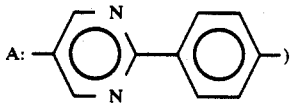

is washed with water and dried: 4.9 g (93%) of colorless crystal of melting point 101°-102° C.;

[α]$_D^{22}$ + 19.6 (c=5, CH$_2$Cl$_2$). 1.5 g (0.004 mol) of this carboxylic acid is purified using 0.65 g (0.005 mol of n-octanol (VI, B: —, R$^2$:C$_8$H$_{17}$), 1.03 g (0.005 mol) of dicyclohexylcarbodiimide and 0.005 g of 4-dimethylaminopyridine in 30 ml of dichloromethane. The mixture is left to stand for 24 hours and filtered, and the filtrate is chromatographed over silica gel using dichloromethane: 1.27 g (68%) of a colorless oil are produced.

[α]$_D^{22}$: +31.6 (c=5, CHCl$_3$).

$^1$H NMR and IR spectra and the elemental analysis support the structure indicated.

B Ethyl (S)-(−)-2-[4-(4-decyloxyphenylcarbonyloxy)-phenyl]oxypropionate (I, R$^1$:C$_{10}$H$_{21}$O,

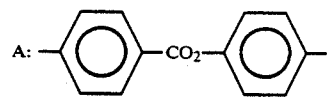

B: —, R$^2$:C$_2$H$_5$)

10 g (0.033 mol) of ethyl (S)-(−)-2-[4-benzyloxyphenyl]oxypropionate (IV, R$^1$:C$_6$H$_5$CH$_2$O-,

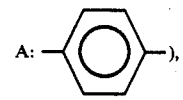

obtained analogously to the above procedure from 4-benzyloxyphenol (I, R$^1$:C$_6$H$_5$CH$_2$O,

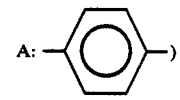

and ethyl (R)-(1)-lactate (III, X:OH) obtained by means of the Mitsonobu reaction, are hydrogenated in 100 ml of tetrahydrofuran by means of 1 g of Pd/C (10%) at 27° C. at atmospheric pressure until the take-up of H$_2$ is complete. The catalyst is filtered off, the solvent is removed by distillation, and 6.5 g of ethyl (S)-(−)-2-(4-hydroxyphenyl)-oxypropionate (IV, R$^1$: —,

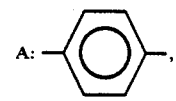

B: —, R$^2$:C$_2$H$_5$),

[α]$^{25}$ (sic): −43.8° (neat), are produced. 8.9 g (0.03 mol) of 4-decyloxybenzoyl chloride are added dropwise to a solution of 6.1 g (0.029 mol) of this compound in 20 ml of pyridine at 10° C. The mixture is stirred for 3 hours at 10° C. and then poured into 200 ml of ice water, adjusted to pH 3 by addition of HCl and extracted with dichloromethane. The extract is chromatographed on silica gel using dichloromethane, and the product-containing fraction is recrystallized from methanol: 4.1 g (40% of theory) of colorless crystals;

[α]$_D^{23}$: −26.1°
(c=1, CHCl$_3$).

The $^1$NMR and IR spectra and the elemental analysis agree with the structure indicated.

When the appropriate educts are used, these procedures for the preparation of compound types A and B from the state of the art are representative of all compounds according to the invention in Table 1.

TABLE I $$R^1-A-O-\overset{CH_3}{\underset{*}{C}H}-CO_2-B-R^2$$

| No. | R¹ | -A- | -B- | -R² | Phase sequence (°C.) K | S_A | N* | I |
|---|---|---|---|---|---|---|---|---|
| 1 | C₈H₁₇ | pyridine-phenyl | — | (S)—CH₂CH(Cl)CH₃ | .32 | — | — | — |
| 2 | " | " | — | (S)—CH(CH₃)C₂H₅ | .−50 | — | — | — |
| 3 | " | " | — | (S)—CH₂CH(CH₃)C₂H₅ | .−50 | — | — | — |
| 4 | C₈H₁₇ | pyridine-phenyl | — | (2S,3S)—CH₂—CH—CH—C₃H₇ (epoxide) | .33 | — | — | — |
| 5 | " | " | phenyl | (R)—OCH(CH₃)CO₂C₂H₅ | .51 | — | — | — |
| 6 | " | " | — | (S)—OCH(CH₃)CO₂C₂H₅ | .69 | — | — | — |
| 7 | C₁₀H₂₁O | phenyl-CO₂-phenyl | " | (S)—CH₂CH(CH₃)C₂H₅ | .9 | — | — | — |
| 8 | C₁₆H₃₃O | phenyl-CO₂-phenyl-CO₂-phenyl | — | " | .44 | — | — | — |
| 9 | C₈H₁₇O | pyridine-phenyl | — | (S)—CH₂CH(CH₃)C₂H₅ | .84 | .93 | .95 | — |
| 10 | " | " | — | (S,S)—CH₂CH(Cl)—CH(CH₃)—C₂H₅ | 25 | — | — | — |

Compounds 1-6 have the R-configuration and compounds 7-10 have the S-configuration at the central asymmetrical carbon atom.

TABLE II

| Comp. from Table I | Mixture with | S*_c range (°C.) | $P_a$ (nC·cm$^{-2}$) | $\tau$ (µs) | $2\theta$ (degrees) | Temp. (°C.) |
|---|---|---|---|---|---|---|
| 1 | A | 11[5]–30 | <5 | <3 | 2 | 25 |
| 2 | A | 10[0]–18 | −10 | 22 | 9 | 5 |
| 3 | A | 11[−3]24 | −10 | <2 | 25 | 20 |
| 4 | A | 13[1]–23 | — | — | — | — |
| 5 | A | 13[5]–42 | +22 | 280 | 33 | 25 |
| 6 | A | 13[10]–41 | +14 | 350 | 40 | 25 |
| 7 | B | 25[24]–55 | −107 | 40 | 46 | 40 |
| 8 | B | 30[30]–58 | −115 | 57 | 57 | 40 |
| 9 | B | 33[32]–58 | −(<5) | 130 | 37 | 40 |
| 10 | B | 25[23]–50 | −110 | 53 | 50 | 40 |

USE EXAMPLES 1 TO 26

In order to test the effectiveness of the above-described compounds as dopes in liquid-crystal systems, they are mixed, in concentrations of 10 mol-% in each case, with the racemates of compounds A or B or the enantiomer C

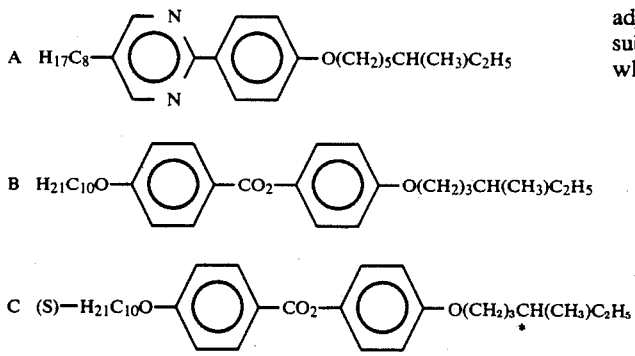

and the values for spontaneous polarization ($P_s$ in nC.cm$^{-2}$), for the switching time $\tau$ (in µs at $+10^7$ Vm$^{-1}$) and for the optical tilt angle of the SmC* phase $\theta$ (in °) of each of the mixtures is determined. $P_s$ values are measured by the method of Sawyer et al. (Phys. Rev. 35, 269 to 273, 1930), a special-purpose measuring cell [Skarp et al. in Ferroelectric Letters, Vol. 06,000 (1986)]being used in which the $\tau$ and $\theta$ values are also determined. At a cell path length of 2 µm, a uniform planar orientation of the liquid crystals in the SmC* phase is achieved by shearing [SSFLC Technique, Clark et al., Appl. Phys. Lett. 36, 899 (1980)]. After placing the measurement cell between two crossed polarizers, the switching time is determined with the aid of a photodiode and/or the optical tilt angle and/or the switching angle by rotating the measuring cell from maximum to minimum light transmission through the measurement arrangement. Table II collates the results for the mixtures. Column 1 gives the number of the compound according to the invention as in Table I, column 2 indicates the mixture component A, B or C, column 3 gives the Smc. (sic) range, the values in parentheses indicating the supercoolable limit of the SmC* range, column 4 gives the spontaneous polarization, column 5 the switching time, column 6 the switching angle and column 7 the measurement temperature.

We claim:

1. A chiral aryloxypropionate of the formula

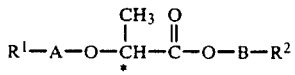

wherein R$^1$ is a straight-chain alkyl or alkoxy of 7 to 16 carbon atoms, A is selected from the group consisting of phenylene, biphenylene, pyrimidylphenyl, phenylcarbonyloxyphenyl and (phenylcarbonyloxy)-phenylcarbonyloxy) phenyl and B is a chemical bond or a phenylene, biphenylene or pyrimidinephenyl and a) if B is a chemical bond, R$^2$ is an alkyl of 2 to 10 carbon atoms which contains an asymmetrical carbon atom substituted by —CH$_3$, halogen or a —COOC$_2$H$_5$ or an alkyl of 3 to 10 carbon atoms which contains two adjacent, asymmetrical carbon atoms of which one is substituted by halogen and the other by a —CH$_3$, or which, together with an O, form an oxirane ring, of (b) if B is one or two aromatic or heteroaromatic rings linked directly to one another, R$^2$ is a chiral alkoxy of 2 to 10 carbon atoms which contains an asymmetrical carbon atom substituted by CH$_3$, halogen or a —COOC$_2$H$_5$ or R$^2$ is an alkoxy of 3 to 10 carbon atoms which contains two adjacent, asymmetrical carbon atoms, of which one is substituted by halogen and the other by a CH$_3$, or which, together with an O-atom form an oxirane ring.

2. A chiral aryloxypropionate of claim 1 wherein (a) if B is a chemical bond, R$^2$ is an alkyl of 2 to 10 carbon atoms which contains an asymmetrical carbon atom substituted by —CH$_3$, halogen or a —COOC$_2$H$_5$, or an alkyl of 3 to 10 carbon atoms which contains two adjacent, asymmetrical carbon atoms of which one is substituted by halogen and the other by a —CH$_3$, or which, together with an O, form an oxirane ring, or (b) if B is one aromatic ring, R$^2$ is a chiral alkoxy having the same number of carbon atoms and the same structure of the alkyl group as under (a).

3. A twistable liquid-crystal phase comprising 2 to 20 components which contains at least one chiral compound of formula I of claim 1.

4. A twistable liquid-crystal phase comprising 2 to 20 components which contains at least one chiral compound of formula I of claim 2.

5. A twistable liquid-crystal phase of claim 3 which contains besides the compound of formula I an ester compound having a S$_c$ phase.

6. A twistable liquid-crystal phase of claim 5 which contains a phenyl 4-alkoxybenzoate as the ester compound having a S$_c$ phase.

7. A twistable liquid-crystal phase of claim 3 which contains, besides the compound of formula I, a phenylpyrimidine compound having a S$_c$ phase.

8. A twistable liquid-crystal phase of claim 2 which contains 4-(5-alkylpyrimidine-2-yl)-1-alkoxybenzene as the phenylpyrimidine compound having a S$_c$.

9. An electrooptical display device containing a liquid-crystal phase of claim 3.

* * * * *